(12) United States Patent
Apffel, Jr.

(10) Patent No.: US 6,607,644 B1
(45) Date of Patent: Aug. 19, 2003

(54) MICROANALYTICAL DEVICE CONTAINING A MEMBRANE FOR MOLECULAR IDENTIFICATION

(75) Inventor: James A. Apffel, Jr., Mountain View, CA (US)

(73) Assignee: Agilent Technolgoies, Inc., Palo Alto, CA (US)

( * ) Notice: Subject to any disclaimer, the term of this patent is extended or adjusted under 35 U.S.C. 154(b) by 260 days.

(21) Appl. No.: 09/703,431

(22) Filed: Oct. 31, 2000

(51) Int. Cl.⁷ .................. G01N 27/447; G01N 27/453
(52) U.S. Cl. ............ 204/451; 204/450; 204/600; 204/601; 422/50
(58) Field of Search ........................ 204/450, 451, 204/600, 601; 422/50, 100

(56) References Cited

U.S. PATENT DOCUMENTS

| 5,556,528 A |   | 9/1996  | Bohn et al. ............. 204/600 |
|---|---|---|---|
| 5,705,813 A |   | 1/1998  | Apffel et al. ............ 250/288 |
| 5,716,825 A |   | 2/1998  | Hancock et al. ........ 435/286.5 |
| 5,993,627 A |   | 11/1999 | Anderson et al. ........ 204/456 |
| 5,997,708 A | * | 12/1999 | Craig .................... 204/601 |
| 6,093,541 A |   | 7/2000  | Nelson ...................... 435/6 |
| 6,103,199 A | * | 8/2000  | Bjornson et al. ........ 422/100 |
| 6,267,859 B1 | * | 7/2001 | Kambara ................. 204/604 |

FOREIGN PATENT DOCUMENTS

| WO | WO95/30892 | 5/1994 | ......... G01N/27/26 |
|---|---|---|---|
| WO | WO99/65945 | 6/1998 | ......... C07K/14/78 |

* cited by examiner

Primary Examiner—Nam Nguyen
Assistant Examiner—Alex Noguerola

(57) ABSTRACT

The invention provides a microanalytical device for analyzing a fluid sample containing at least one analyte molecule. The device is constructed from a substrate and a cover plate each having a substantially planar surface and a microchannel formed therein. The cover plate is placed over the substrate such that the cover plate microchannel is arranged in opposing relationship with the substrate microchannel. A membrane is interposed between the substrate and the cover and has at least one pore sized to allow passage of the analyte molecule from the substrate microchannel to the cover plate microchannel. An analyte altering moiety is attached to an interior surface of the pore and is capable of chemically altering the analyte molecule. Also disclosed are a method for chemically altering and transporting an analyte molecule in a fluid and a method for identifying a plurality of biomolecules.

30 Claims, 6 Drawing Sheets

MICROANALYTICAL DEVICE CONTAINING A MEMBRANE FOR MOLECULAR IDENTIFICATION

TECHNICAL FIELD

The present invention relates generally to microanalytical devices for use in analysis of complex molecules and biomolecules, and more specifically, to microanalytical devices containing a membrane for biomolecular identification.

BACKGROUND

There is a rapidly growing awareness of the importance of biomolecular identification in the discovery of medically important proteins and the genes from which they derive, e.g., proteomics and genomics. For example, many of the best-selling drugs today either are proteins or act by targeting proteins. In addition, many molecular markers of disease, the basis of diagnostics, are peptidic or nucleotidic sequences. It is evident that biomolecular identification techniques such as proteomics and genomics have major implications for pharmaceutical research and development.

Biomolecular identification often involves the analysis of large complex biomolecules, typically peptidic biomolecules such as proteins in the case of proteomics, by breakdown thereof into simpler component substances. Two-dimensional electrophoresis technology forms a current basis of the expanding field of proteomics in large part because of the high resolution obtainable from multidimensional separation. For example, two-dimensional electrophoresis has been widely used to separate hundreds to thousands of proteins in a single analysis, in order to determine the protein composition of biological samples such as blood plasma, tissues, cultured cells, etc. Such two-dimensional procedures may involve sequential separations by isoelectric focusing and slab gel electrophoresis followed by mass spectrometry. However, this technology suffers from its slow and labor-intensive nature. Thus, automation of the procedure is desired for scale-up of efforts to build proteome databases comprising all the proteins of complex organisms such as human beings. For instance, U.S. Pat. No. 5,993,627 to Anderson et al. discloses an automatic system for two-dimensional electrophoresis. However, this system is complex in design and is likely to require a large amount of sample for proper functioning. Not surprisingly, two-dimensional electrophoresis is still ordinarily performed by hand or on a bench scale level.

Other automated approaches may also enhance the speed of analysis. One such approach involves the use of devices capable of carrying out analysis such as multidimensional liquid chromatography-mass spectrometry. For example, U.S. Pat. No. 5,705,813 to Apffel et al. describes an integrated planar liquid handling system for matrix-assisted laser-desorption ionization time-of-flight (MALDI-TOF) mass spectrometry. The patent discloses that a reservoir for receiving fluid substances may be interconnected by a microchannel to a MALDI ionization surface, wherein the microchannel comprises a separation region. The separation region may be used for chromatographic-type separations. As another example, U.S. Pat. No. 5,716,825 to Hancock et al. describes an integrated nucleic acid analysis system for MALDI-TOF mass spectrometry. However, the advantages obtained from such high speed analysis are offset by lack of resolution and specificity.

These automated approaches represent recent progress in microfabricated devices used, e.g., as chemical analysis tools or clinical diagnostic tools. Their small size allows for the analysis of minute quantities of sample, which is an advantage where the sample is expensive or difficult to obtain. See, e.g., U.S. Pat. No. 5,500,071 to Kaltenbach et al., U.S. Pat. No. 5,571,410 to Swedberg et al., and U.S. Pat. No. 5,645,702 to Witt et al. Sample preparation, separation and detection compartments have been proposed to be integrated on such devices. Because such microfabricated devices have a relatively simple construction, they are generally inexpensive to manufacture. Nevertheless, the production of such devices present various challenges. For example, the flow characteristics of fluids in the small flow channels of a microfabricated device may differ from the flow characteristics of fluids in larger devices, as surface effects come to predominate and regions of bulk flow become proportionately less. Thus, motive force means for producing a motive force that moves analytes and fluids may have to be incorporated into such microanalytical devices. This may involve forming motive force means such as electrodes on such microanalytical devices which may add to the cost of the device. Moreover, microanalytical devices have never been constructed that have the high resolution capabilities of two-dimensional electrophoresis as a whole.

Another approach in controlling flow characteristics in fluids is to employ membranes having structures with field responsive permeation control. Such structures have been described in a number of patents and publications and may be incorporated into microporous membranes. U.S. Pat. No. 5,556,528 to Bohn et al., for example, describes structures with field response permeation control. A support is interposed in a passageway between a fluid source with target molecules therein and a fluid reservoir, wherein the support permits target molecules to diffuse therethrough. The surface of the support carries at least one monomolecular layer which forms, in part or in whole, an active control structure. The active control structure is an admixture of molecular species, a majority of which has a large ground state dipole moment. The monomolecular layers have closely packed, dipolar molecules that are substantially aligned along their long axes. When an electric field is applied or removed, the permeability of the active control structure is altered. The target molecules are captured or dispensed according to the permeability value. Similarly, International Publication No. WO 99/65945 describes force-regulated molecular recognition switches for controlling binding and release of a ligand to a device containing such a switch. However, such structures have not been used to chemically modify, or more specifically, to cleave, digest, or otherwise segment analyte biomolecules into separate components.

Accordingly, there is a need for a device that requires only small volumes of sample fluid for biomolecular identification applications, particularly proteomics and genomics. In addition, there is a need to maintain high resolution with high speed analysis by allowing parallel chemical alteration, e.g., proteolytic processing, of samples in a microfluidic system.

SUMMARY OF THE INVENTION

Accordingly, it is an object of the present invention to overcome the above-mentioned disadvantages of the prior art by providing a microanalytical device containing a membrane for biomolecular identification.

It is another object of the invention to provide such a device that allows biomolecular identification to be carried out with speed, high resolution and specificity.

It is still another object of the invention to provide such a microanalytical device for biomolecular identification through spatial resolution and digestion.

It is a further object of the invention to provide a method for biomolecular identification using such a microanalytical device.

Additional objects, advantages and novel features of the invention will be set forth in part in the description that follows, and in part will become apparent to those skilled in the art upon examination of the following, or may be learned by practice of the invention.

In a general aspect, then, the present invention relates to a microanalytical device for analyzing a fluid sample containing at least one analyte molecule. The microanalytical device is constructed from a substrate, a cover plate and a membrane. The substrate has a substantially planar substrate surface and a substrate microchannel formed thereon. The cover plate has a substantially planar cover plate surface and a cover plate microchannel formed thereon. The cover plate surface is arranged over the substrate surface, and the membrane is interposed between the substrate and the cover plate. The membrane has at least one pore sized to allow passage of the analyte molecule from the substrate microchannel to the cover plate microchannel. An analyte altering moiety is attached to an interior surface of the at least one pore and is capable of chemically altering the analyte molecule.

In another general aspect, the invention relates to a method for chemically altering and transporting an analyte molecule in a fluid. The method involves providing a substrate having a substantially planar substrate surface, the substrate having a substrate microchannel formed in the substrate surface. The analyte molecule is transported from the substrate microchannel in a non-parallel direction with respect to the substrate surface into a pore of a membrane. Once inside the pore, the analyte molecule is chemically altered using a moiety attached to an interior surface of the pore to form an altered molecule. The altered molecule is collected from the pore on a cover plate microchannel formed on a substantially planar cover plate surface of a cover plate, wherein the substantially planar cover plate surface is in opposing relation to the substantially planar substrate surface.

In a further general aspect, the invention relates to a method for identifying a plurality of biomolecules. First, a substrate having a substantially planar substrate surface is provided having a substrate microchannel formed therein, and the to biomolecules are spatially resolved along the substrate microchannel. Then the biomolecules are transported from the substrate microchannel in a non-parallel direction with respect to the substrate surface into pores of a membrane while preserving the spatial resolution of the biomolecules. There, the biomolecules are digested to form biomolecular components. The biomolecular components, still spatially resolved, are then collected from the pores on a cover plate microchannel channel formed on a substantially planar cover plate surface of a cover plate, wherein the substantially cover plate surface is in opposing relation to the substantially planar substrate surface. Finally, the biomolecular components are spatially resolved in the cover plate microchannel.

BRIEF DESCRIPTION OF THE DRAWINGS

FIG. 1 illustrates an ordinary microanalytical device that is comprised of a substrate having a surface with a microchannel thereon and a cover plate. FIG. 1A illustrates the device in an open form wherein the substrate and the cover plate are separated, thereby exposing the recess on the substrate surface. FIG. 1B illustrates the microanalytical device of FIG. 1A in a closed form wherein the cover plate is aligned with and placed against the surface of the substrate, the cover plate, in combination with the microchannel forms a column. FIG. 1C illustrates in cross-sectional view the microanalytical device illustrated in FIG. 1B.

FIG. 2 illustrates a microanalytical device comprised of a substrate having a surface with a substrate microchannel thereon, a cover plate having a cover plate microchannel thereon and a membrane having a plurality of pores therethrough. FIG. 2A illustrates the device in an open form wherein the substrate is separated from the cover plate, thereby exposing the microchannels on the substrate and cover plate. FIG. 2B illustrates the microanalytical device of FIG. 2A in a closed form wherein the cover plate microchannel is aligned in parallel and opposing relation with the substrate microchannel and the membrane is interposed between the cover plate and the substrate. FIG. 2C illustrates the device in cross-sectional view along the aligned microchannels.

FIG. 3 illustrates a microanalytical device comprised of a substrate and a cover plate each having a surface with a first-dimension microchannel thereon. A plurality of second-dimension microchannels, also on the cover plate and substrate surfaces, fluidly communicate with the first-dimension microchannels. Also provided is a membrane having a plurality of pores therethrough. FIG. 3A illustrates the device in an open form wherein the substrate is separated from the cover plate, thereby exposing the microchannels on the substrate and cover plate. FIG. 3B illustrates the microanalytical device of FIG. 3A in a closed form wherein the second-dimension cover plate microchannels are aligned in opposing relation with the second-dimension substrate microchannels and the membrane is interposed between the cover plate and the substrate.

DETAILED DESCRIPTION OF THE INVENTION

Definitions and Overview

Figure 1A:
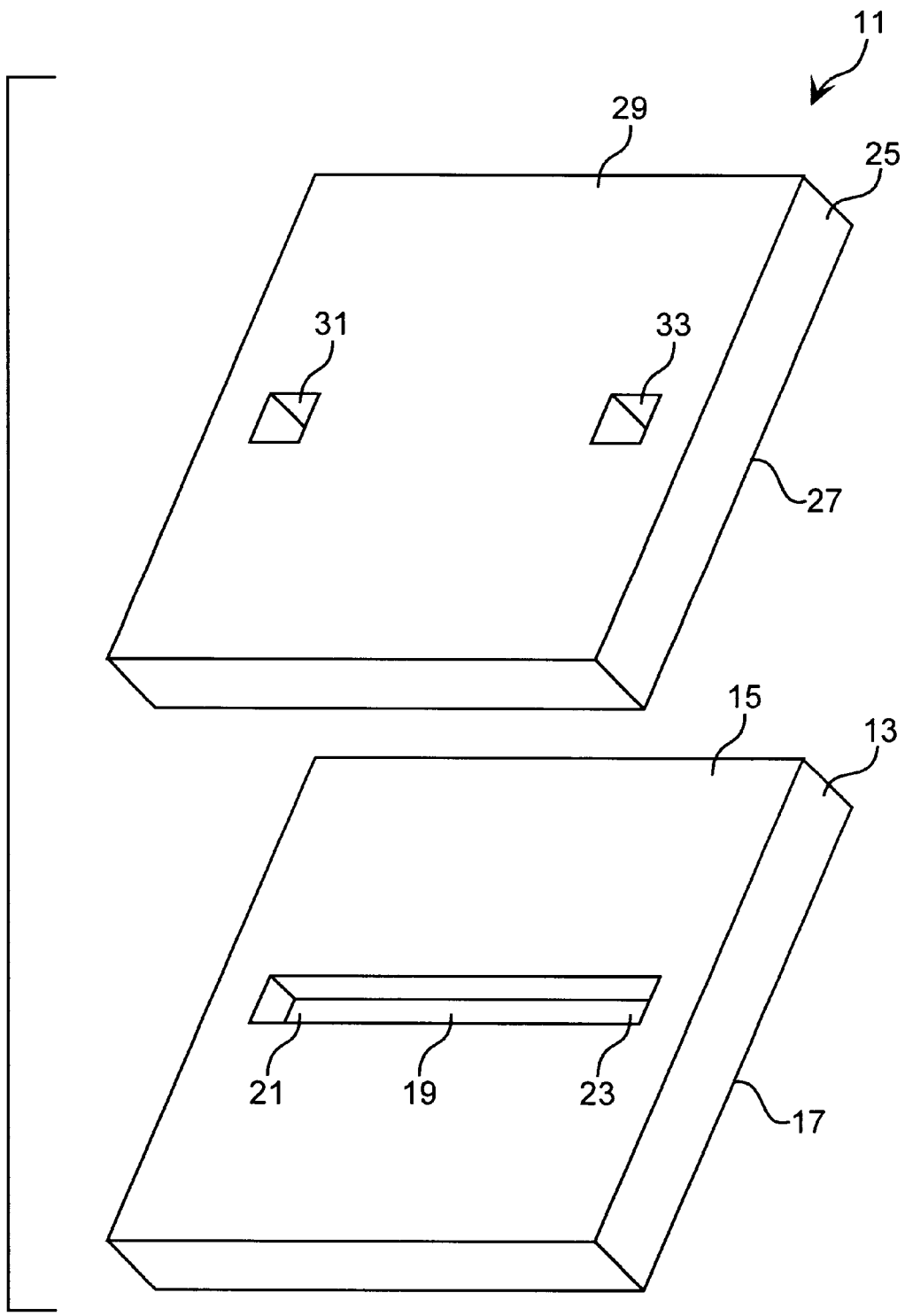
FIGS. 1A, 1B, and 1C, collectively referred to as FIG. 1, illustrate a prior art device.

Before describing the present invention in detail, it is to be understood that, unless otherwise indicated, this invention is not limited to device structures, particular materials or manufacturing processes, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to "a molecule" includes mixtures of molecules, reference to "a microchannel" includes multiple microchannels, and the like.

In describing and claiming the present invention, the following terminology will be used in accordance with the definitions set out below.

The term "chemically altering" is used to refer to a process in which one or more substances are changed chemically into one or more different substances. The process necessarily implies the addition and/or loss of one or more atoms by the substance that is chemically altered. Examples of processes encompassed by chemical altering include, but are not limited to, enzymatic digestion, oxidation, reduction, ionizing, cracking, and labeling.

The term "embossing" is used to refer to a process for forming polymer, metal or ceramic shapes by bringing an embossing die into contact with a pre-existing blank of polymer, metal or ceramic. A controlled force is applied between the embossing die and the pre-existing blank of material such that the pattern and shape determined by the embossing die is pressed into the pre-existing blank of polymer, metal or ceramic. The term "embossing" encompasses "hot embossing" which is used to refer to an embossing process in which the pre-existing blank of material is heated such that it conforms to the embossing die as a controlled force is applied between the embossing die and the pre-existing blank. The resulting polymer, metal or ceramic shape is cooled and then removed from the embossing die.

The term "function" is used herein to describe the operating characteristic of a sample treatment component, e.g., a microchannel or a membrane. The term "function" encompasses, e.g., extraction, filtration, precipitation, derivatization, digestion, concentration of a sample from a dilute solution, chemical alteration of sample components and chromatographic and/or electrophoretic bulk separation of sample components.

The term "injection molding" is used to refer to a process for molding plastic or nonplastic ceramic shapes by injecting a measured quantity of a molten plastic or ceramic substrate into dies (or molds). In one embodiment of the present invention, miniaturized devices can be produced using injection molding.

The term "LIGA process" is used to refer to a process for fabricating microstructures having high aspect ratios and increased structural precision using synchrotron radiation lithography, galvanoforming, and plastic molding. In a LIGA process, radiation sensitive plastics are lithographically irradiated with high energy radiation using a synchrotron source to create desired microstructures (such as channels, ports, apertures, and microalignment means), thereby forming a primary template.

The term "microalignment means" is defined herein to refer to any means for ensuring the precise microalignment of microfabricated features in a microanalytical device. Microalignment means can be formed either by laser ablation or by other methods of fabricating shaped pieces well known in the art. Representative microalignment means that can be employed herein include a plurality of co-axially arranged apertures microfabricated in component parts and/ or a plurality of corresponding features substrates, e.g., projections and mating depressions, grooves and mating ridges or the like. Alternative alignment means includes, but are not limited to, features forms in component parts such as pin and mating aperture.

The term "microanalytical device" refers to a device having features of micron or submicron dimensions, and which can be used in any number of chemical processes involving very small amounts of fluid. Such processes include, but are not limited to, electrophoresis (e.g., CE or MCE), chromatography (e.g., $\mu$LC), screening and diagnostics (using, e.g., hybridization or other binding means), and chemical and biochemical synthesis. The features of the microanalytical devices are adapted to the particular use. For example, microanalytical devices that are used in separation processes, e.g., MCE, contain microchannels on the order of 1 $\mu$m to 200 $\mu$m in diameter, typically 10 $\mu$m to 75 $\mu$m in diameter, and approximately 0.1 to 50 cm in length and have a volume of about 1 $\mu$l to about 500 $\mu$l, typically about 10 $\mu$l to 200 $\mu$l.

The term "membrane" is used herein in its ordinary sense and refers to a thin sheet of permeable material having at least one pore which provides a passage for an analyte molecule through the sheet. Typically, membranes of the present invention have a thickness of about 10 angstroms to about 500 angstroms, preferably of about 10 angstroms to about 100 angstroms and optimally of about 20 to about 100 angstroms.

The term "motive force" is used to refer to inducing movement of a sample along a column or a microchannel usually in a liquid phase analysis, and includes, e.g., application of an electric potential across any portion of the column, application of a pressure differential across any portion of the column or any combination thereof. Accordingly, a "motive force means" is any means capable of producing a motive force. For example, electrodes may represent motive force means for applying an electric potential across a portion of a microchannel.

"Optional" or "optionally" as used herein means that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The invention thus provides a microanalytical device for analyzing a fluid sample containing at least one analyte molecule and represents an improvement over previously known sample introduction devices. The device is constructed from a substrate and a cover plate each having a substantially planar surface and a microchannel formed thereon. The cover plate is placed over the substrate such that the cover plate microchannel is arranged in opposing relationship with the substrate microchannel. A membrane is interposed between the substrate and the cover and has at least one pore sized to allow passage of the analyte molecule from the substrate microchannel to the cover plate microchannel. An analyte altering moiety is attached to an interior surface of the pore. The moiety is capable of chemically altering the analyte molecule. The invention is particularly useful for separating a plurality of different biomolecules in a fluid and for identifying each of the biomolecules of the plurality.

Figure 1B:
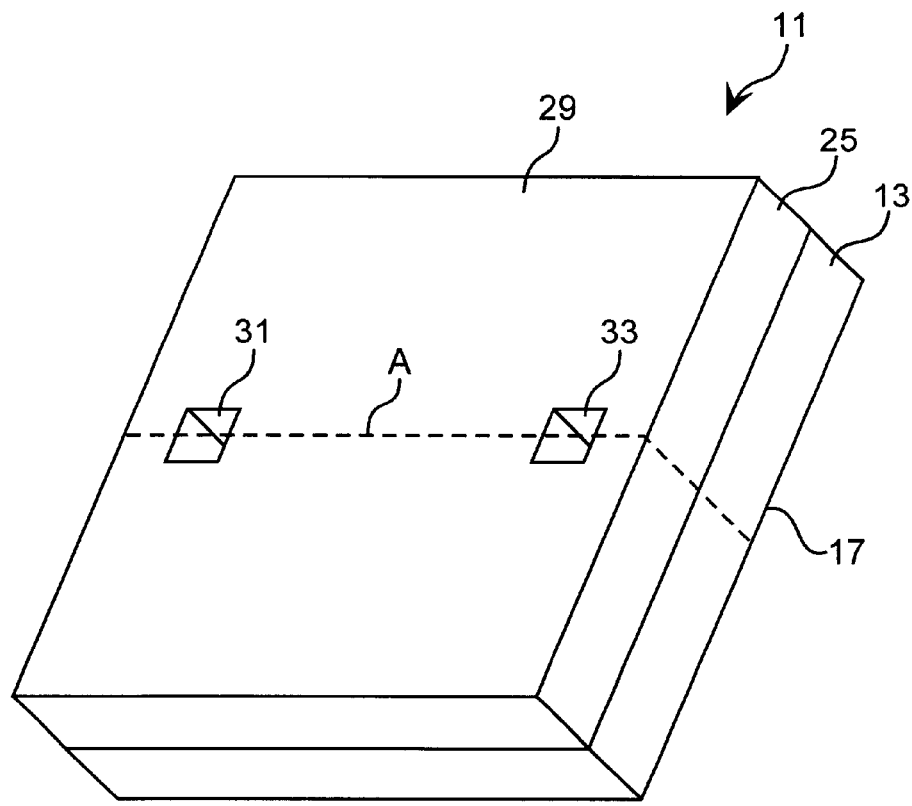
Figure 1C:
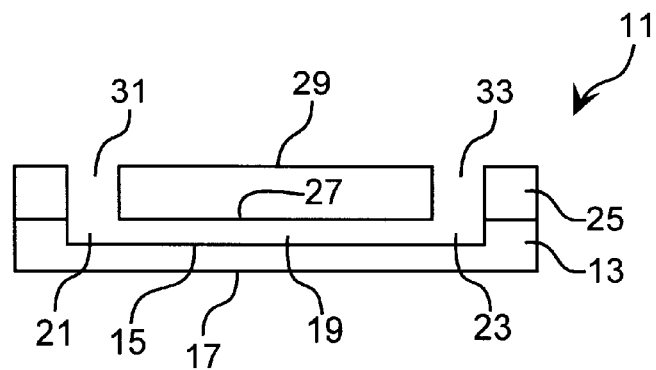

To provide an example of a prior art device and to illustrate the disadvantages associated therewith, FIG. 1 schematically illustrates a microanalytical device for separating analyte molecules. FIG. 1A illustrates the microanalytical device in an open unassembled form. FIG. 1B illustrates the microanalytical device that is ready for use in its closed form. FIG. 1C illustrates a cross sectional view, indicated by dotted line A, of the microanalytical device illustrated in FIG. 1B. As with all figures referenced herein, in which like parts are referenced by like numerals, FIG. 1 is not to scale, and certain dimensions may be exaggerated for clarity of presentation. Referring now to FIG. 1A, the prior art device is generally represented at 11, comprising substrate 13 having first and second substantially planar opposing surfaces indicated at 15 and 17, respectively, and a substrate microchannel 19 in the form of a shallow recess on the first substrate surface 15. The substrate microchannel 19 has a sample inlet terminus 21 at one end and a downstream terminus 23 at another end.

The microanalytical device also includes a cover plate 25 having first and second substantially planar opposing surfaces indicated at 27 and 29. A sample inlet port 31 and an outlet port 33 are also provided, each in the form of an aperture extending through the cover plate. The closed form of the prior art microanalytical device is shown in FIG. 1B.

Before use, the cover plate is placed over the substrate such that the underside surface 27 of the cover plate is positioned in opposing relationship with the first substrate surface, as illustrated in FIG. 1B. In addition, the cover plate and the substrate are aligned to provide fluid communication between the sample inlet port and the sample inlet terminus of the microchannel as well as fluid communication between the sample outlet port with the downstream terminus of the microchannel. Closure of the device by aligning the cover plate with the substrate and forming a seal therebetween results in formation of a microcolumn into which fluids may be introduced through inlet port 31 and removed through outlet port 33. Usually, a liquid-tight seal is formed between the cover plate and the substrate.

In operation, one or more fluids containing analyte molecules are introduced into the column from an external source through inlet port 27. Sample movement within the column may be induced by a motive force produced by one or more motive force means (not shown). Outlet port 29 enables passage of fluid from the microcolumn to the exterior of the microanalytical device. The column is adapted to separate the analyte molecules according to one or more properties, e.g., by polarity. In the case of separation by polarity, analyte molecules become spatially resolved by polarity as the sample fluid flows through the column, as shown in FIG. 1C. As a result, analyte molecules passing through the outlet port will tend become grouped by either increasing or decreasing polarity. Fluid passing through the outlet port may be then introduced into another device, e.g., a mass spectrometer for further analysis. This approach suffers from a number of drawbacks, the most notable being the lack sufficient resolution and/or specificity. Using separation by polarity as an example, different analyte molecules may have similar polarities. Thus, fluid emerging from the sample outlet port may contain a mixture of different analyte molecules having the same polarity. Without more analysis, it may not be possible to distinguish whether the emerging fluid is single analyte or a mixture of different analytes. It is evident, then, that this prior art device lacks specificity and resolution for molecular identification.

Figure 2A:
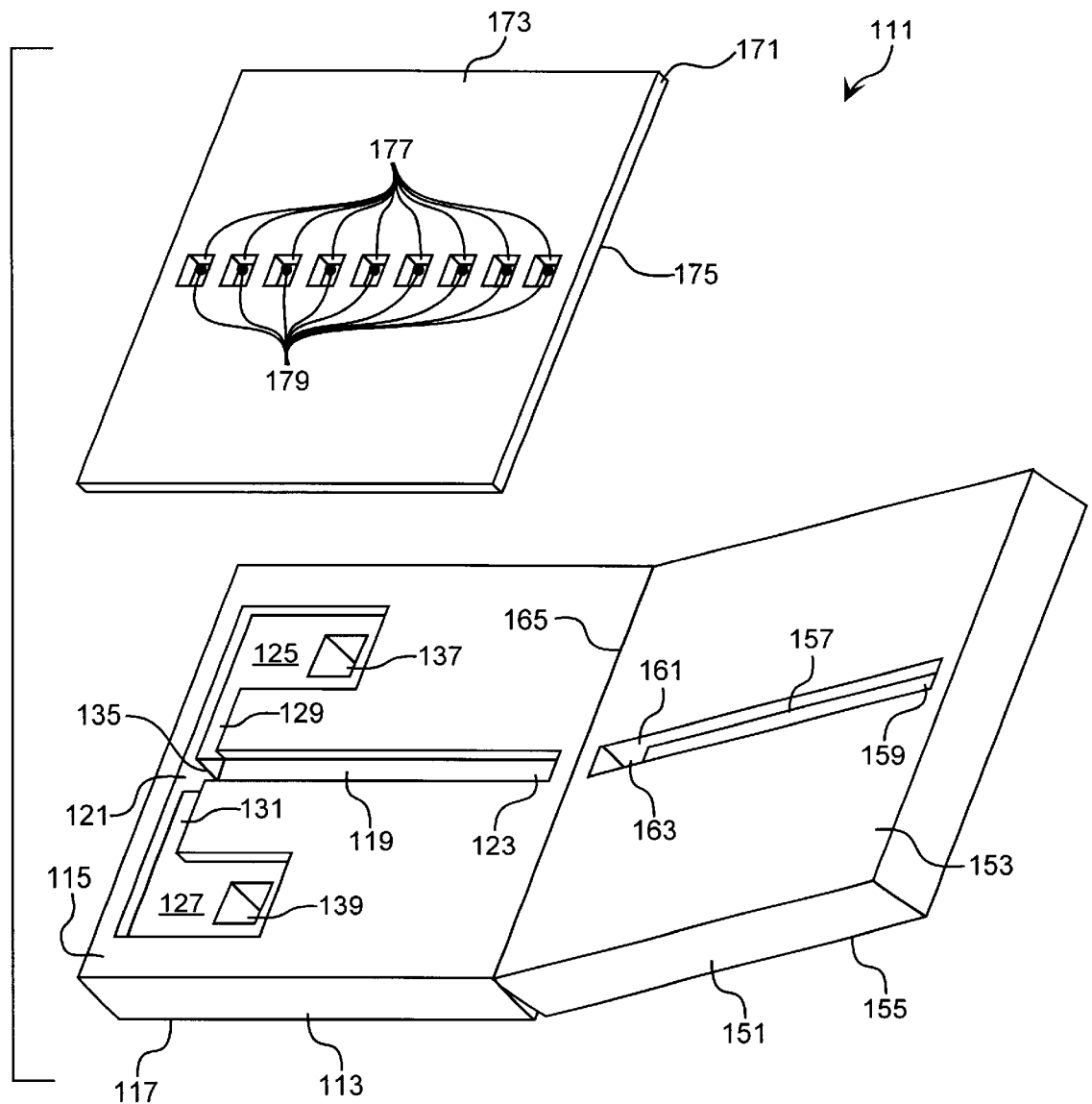
FIGS. 2A, 2B and 2C, collectively referred to as FIG. 2, illustrate an embodiment of the present invention.
Figure 2B:
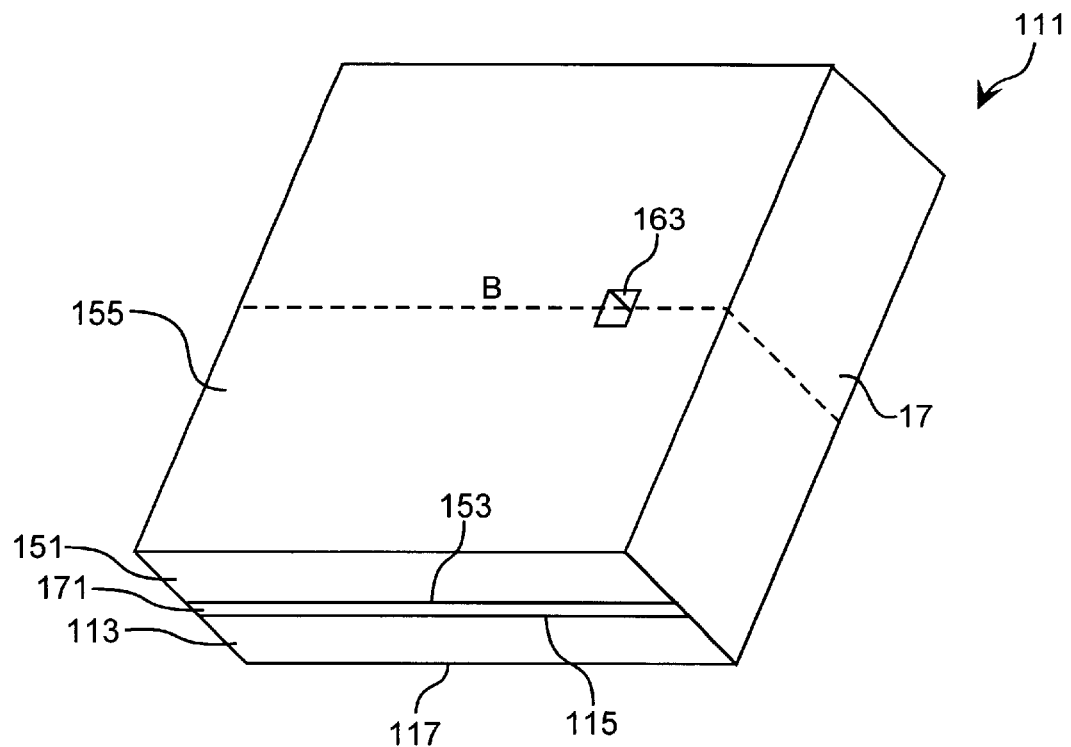
Figure 2C:
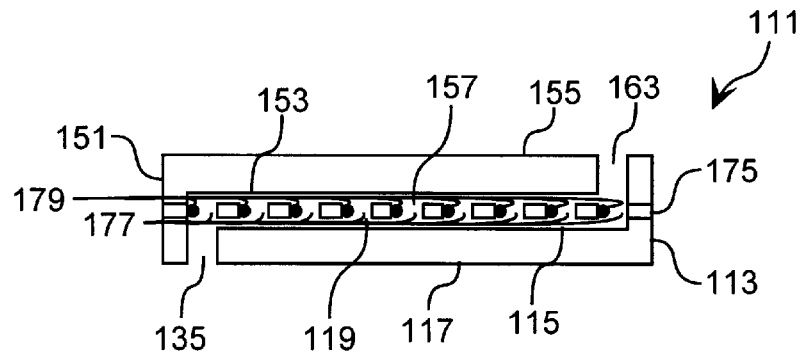

One embodiment of the present invention is represented in FIG. 2 which illustrates a microanalytical device that can be used in conducting a chemical alteration process such as analyzing a fluid containing an analyte. FIG. 2A illustrates the microanalytical device in an open unassembled form. FIG. 2B illustrates the microanalytical device in its ready-for-use closed form. FIG. 2C illustrates a cross sectional view indicated by dotted line B of the microanalytical device illustrated in FIG. 2B. Referring now to FIG. 2A, the device is generally represented at 11. One component of the device is a substrate 113 having first and second substantially planar opposing surfaces indicated at 115 and 117, respectively. A substrate microchannel 119 in the form of a shallow recess, i.e., a recess having a depth of micron or even submicron dimensions, is located on the first substrate surface 115. It will be readily appreciated that although the substrate microchannel 119 has been represented in a generally extended form, microchannels formed in the practice of the invention can be in a large variety of configurations, such as in a straight, serpentine, spiral, or any tortuous path desired. Further, the substrate microchannel 119 can be formed in a wide variety of channel geometries including semi-circular, rectangular, rhomboid, and the like, and the microchannels can be formed in a wide range of aspect ratios. In other words, the dimensions and the shape of the recess are generally limited only by the dimension of the substrate. It is also noted that a substrate having a plurality of microchannels thereon falls within the spirit of the invention. The substrate microchannel 119 has a sample inlet terminus 121 at one end and a downstream terminus 123 at another end. Optionally, the first planar surface 115 further includes on-device reservoir means 125 and 127, each formed from a cavity in the first planar surface 115. Like the microchannel, each cavity can be formed in any geometry and with any aspect ratio, limited only by the overall thickness of the substrate 113, to provide reservoir means 125 and 127 each with a desired volume. The reservoir means can be used, individually or in combination, to provide, e.g., a makeup flow fluid or a fluid regulation function. As shown, each of the reservoir means is in fluid communication with the substrate microchannel 119 through reservoir microchannels 129 and 131 in the first planar surface 115. A sample inlet port 135 is provided fluid communication with the sample inlet terminus 121 of the substrate microchannel and is in the form of an aperture that extends through the substrate. Similarly, reservoir ports 137 and 139 may also be provided for fluid communication with the reservoir means 125 and 127, respectively.

The microanalytical device also includes a cover plate 151 having first and second substantially planar opposing surfaces indicated at 153 and 155, respectively. A cover plate microchannel 157 is located on the underside surface 153. Like the substrate microchannel, the cover plate microchannel 157 is shown in a generally extended form and has an upstream terminus 159 at one end and a sample outlet terminus 161 at another end. The length of the cover plate microchannel 157 corresponds to the length of the substrate microchannel 119. The cover plate microchannel generally represents a mirror image of the substrate microchannel. As such, each location in the cover plate microchannel has a corresponding location on the substrate microchannel. An outlet port 163 is provided fluid communication with the sample outlet terminus 161 and is in the form of an aperture that extends through the cover plate.

As shown in FIG. 2, the substrate 113 and the cover plate 151 are formed in a single, solid piece that may or may not be flexible. The substrate and the cover plate are separated by at least one fold means, generally indicated at 165, such that the first substrate surface 115 and the underside cover plate surface 153 can be readily folded to overlie each other in opposing relation. The fold means can comprise a row of spaced-apart perforations in the substrate, a row of spaced-apart slot-like depressions or apertures that extend only part way through the substrate, or the like. The perforations or depressions can have circular, diamond, hexagonal or other shapes that promote hinge formation along a predetermined straight line. The fold means 165 serves to align the cover plate 151 with the substrate 113. Alternatively, the cover plate and the substrate may be formed from a discrete and separate components. However, a discrete cover plate and substrate construction may require microalignment means described herein or known to one of ordinary skill in the art in order to align the cover plate with the substrate.

The microanalytical device also includes a membrane 171 having two substantially opposing surfaces, i.e., a cover plate-side surface 173 and a substrate-side surface 175. The membrane has at least one pore sized to allow passage of an analyte molecule from the substrate microchannel 119 to the cover plate microchannel 157. Preferably, as shown in FIG. 2A, the membrane has a plurality of pores 177 arranged in an array and each sized and shaped to allow passage of analyte molecules from one membrane surface to the other. An analyte altering moiety 179 is attached to an interior surface of the at least one pore, or as shown, in each of the pores, wherein the moiety is capable of chemically altering the analyte molecule while the analyte molecule is passing though the pore. For example, the analyte altering moiety may be adapted to digest the analyte molecule to form at least two analyte components as is discussed below.

The closed form of the microanalytical device is shown in FIG. 2B. Before use of the device, the cover plate 151 is placed over the substrate such that the underside surface 153 of the cover plate is positioned in opposing relationship with the first substrate surface 115, as illustrated in FIG. 2B. Interposed between the cover plate 151 and the substrate 113 is the membrane 171.

FIG. 2C illustrates in cross-sectional view along the aligned microchannels of the microanalytical device illustrated in FIG. 2B. As shown, the cover plate 151 and the substrate 113 are aligned to provide fluid communication between the substrate microchannel 119 and cover plate microchannel 157 through the pores 177 of the membrane 175. Usually, a liquid-tight seal is formed between the cover plate, the membrane and the substrate such that fluid is confined to the microchannels and the pores of the membrane. In operation, a fluid containing at least one analyte molecule is introduced from an external source through inlet port 135 into the substrate microchannel 119. Sample movement within the substrate microchannel 119 may be induced by using any number of motive force means, not shown, to produce a motive force. Likewise, sample movement through the pores 179 of the membrane and within the cover plate microchannel 157 may also be induced through application of one or more motive forces. Outlet port 163 enables passage of fluid from the cover plate microchannel 157 to the exterior of the microanalytical device.

Once sample is introduced into the substrate microchannel through the inlet port 135, the substrate microchannel 119 may perform one or more functions. For example, the microchannel may serve merely as a conduit through which sample fluid flows. In the alternative, the microchannel may be additionally adapted to perform a separation function, e.g., in order to sort analyte molecules according to particular property, e.g., molecular weight. In such a case, the molecular weight of the analyte molecules decreases along the length of the substrate microchannel. In other words, analyte molecules become spatially resolved by molecular weight as the sample fluid flows through the substrate microchannel. The pores in the membrane allow fluid from the substrate microchannel to be conveyed to the cover plate microchannel in a direction orthogonal to the substrate microchannel. When fluid is conveyed from the substrate microchannel to the cover plate microchannel, analyte molecules are altered by the attached analyte altering moiety. However, the altered analyte molecules in the cover plate microchannel remain spatially resolved in a manner that corresponds the spatial resolution in the substrate. Thus, in effect, spatial resolution of analyte molecules is preserved while the analyte molecules are chemically modified.

The device allows varying types of chemical modification. For example, each of the pores in the membrane may have an inner surface attached to which is an analyte altering moiety adapted to attach a label to the analyte molecule passing through the pore. Thus, when fluid is conveyed from the substrate microchannel to the cover plate microchannel, analyte molecules are labeled by the attached moiety. However, the altered analyte molecules in the cover plate microchannel remain spatially resolved in a manner that corresponds to the spatial resolution in the substrate. Thus, in effect, the labeled analyte molecules retain their original spatial resolution. In addition, the cover plate microchannel may serve merely as a conduit through which sample fluid flows. In such a case, spatially-resolved labeled analyte molecules may be sequentially delivered to an apparatus adapted to detect the labeled analyte molecules by employing a motive force that moves each of the labeled analyte molecules in the same manner.

Moreover, the device may be adapted to perform a number of functions to increase the overall analytical capability of the device. For example, each of the pores in the membrane may have an inner surface attached to which is a moiety adapted to digest the analyte molecule passing through the pore. Thus, after analyte molecules are spatially resolved with respect to polarity, the analyte molecules are conveyed from the substrate microchannel through the pores, where they are digested by the attached moiety to form digested analyte components. Then, the digested analyte components are transported to the cover plate microchannel while retaining spatial resolution. The digested analyte components for each analyte may be further resolved if the cover plate microchannel is adapted to perform another resolution function, e.g., separating molecules by polarity. In such a case, spatially-resolved analyte components for each analyte may be sequentially delivered by polarity to an apparatus. In addition, since the molecules are spatially resolved before digestion, the device can also be adapted to maintain the spatial resolution of the components for different analyte molecules. In other words, microanalytical devices in this configuration analyze for both molecular weight of analyte molecules and for polarity of the components of the molecules. In any case, once the analyte is conveyed into the cover plate microchannel, the microchannel may then be eluted to a detection system. Depending on the type of detection desired, the detection system may employ one of any number of analysis such as mass spectrometry or other analytical techniques known to one of ordinary skill in the art.

Figure 3A:
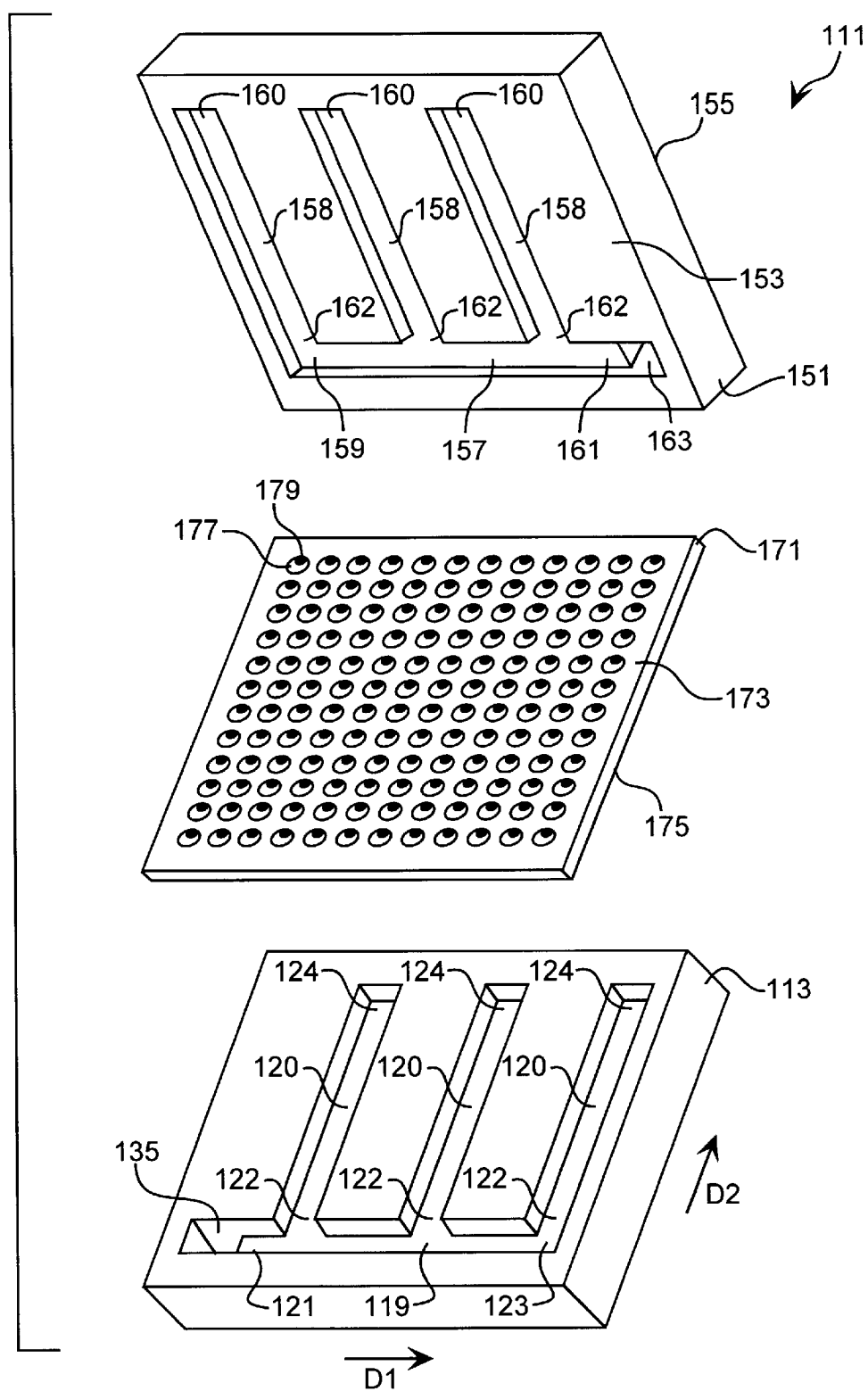
FIGS. 3A and 3B, collectively referred to as FIG. 3, illustrate still another embodiment of the present invention.
Figure 3B:
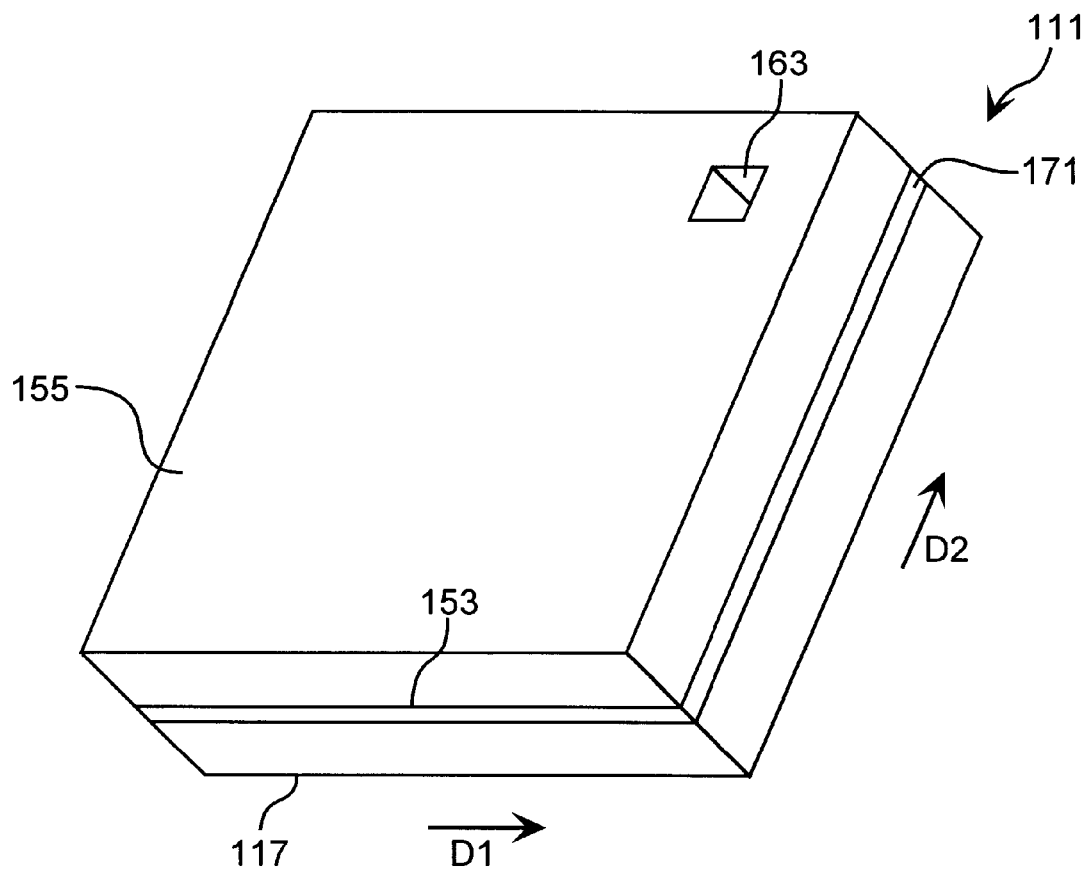

FIG. 3 illustrates a more complex version of the inventive microanalytical that may be particularly useful in conducting a separation process. FIG. 3A illustrates the microanalytical device in an open unassembled form. FIG. 3B illustrates the microanalytical device in its ready-for-use closed form. Referring now to FIG. 3A, the device is generally represented at 111, providing a substrate 113 having first and second substantially planar opposing surfaces indicated at 115 and 117, respectively, and a first-dimension substrate microchannel 119 in the form of a shallow recess on the first substrate surface 115. The first-dimension substrate microchannel 119 has a sample inlet terminus 121 at one end and a downstream terminus 123 at another end. A sample inlet port 135 is provided fluid communication with the sample inlet terminus 121 of the first-dimension substrate microchannel and is in the form of an aperture that extends through the substrate. Also located on the first substrate surface 115 and fluidly communicating with the first-dimension substrate microchannel along its length are a number of second-dimension substrate microchannels 120. As shown in FIG. 3A, each of the second-dimension substrate microchannels 120 also has an upstream terminus 122 that begins at the first-dimension substrate microchannel 119 and a downstream terminus 124 that terminates blindly. In addition, each of the second-dimension substrate microchannels are substantially the same length and parallel to each other.

The microanalytical device also includes a cover plate 151 having first and second substantially planar opposing surfaces indicated at 153 and 155, respectively, and a first-dimension cover plate microchannel 157 on the underside surface 153. The first-dimension cover plate microchannel 157 is shown in a generally extended form and has an upstream terminus 159 at one end and a sample outlet terminus 161 at another end. Also provided are a number of second-dimension cover plate microchannels 158, one for each second-dimension substrate microchannel. The second-dimension cover plate microchannels 158 are arranged to correspond with the second-dimension substrate microchannels 120 and form a mirror image of the second-dimension substrate microchannels. As such, each second-dimension cover plate microchannel has a corresponding second-dimension substrate microchannel. In addition, each second-dimension cover plate microchannel begins blindly at an upstream terminus 160 and fluidly communicates with the first-dimension cover plate microchannel 157 at a downstream terminus 162. An outlet port 163 is provided in fluid communication with the sample outlet terminus of the 161 and is in the form of an aperture that extends through the cover plate.

Unlike the microanalytical device illustrated in FIG. 2, the substrate and the cover plate illustrated in FIG. 3 represent discrete components, i.e., the substrate is separate from the cover plate. Interposed between the cover plate and the substrate is a membrane 171 having two substantially opposing surfaces, i.e., a cover plate-side surface 173 and a substrate-side surface 175. As shown in FIG. 3A, the membrane has a plurality of pores, one of which is indicated at 177, arranged in an array and sized to allow passage of analyte molecules from one membrane surface to the other. An analyte altering moiety, one of which is indicated at 179, is attached to an interior surface of each of the pores, wherein the moiety is capable of chemically altering the analyte molecule while the analyte molecule is passing though the pore. Again, the analyte altering moiety may be adapted to digest the analyte molecule to form at least two analyte components as is discussed below.

The closed form of the microanalytical device is shown in FIG. 3B. Prior to use of the device, the cover plate 151 is placed over the substrate 113 such that the underside surface 153 of the cover plate is positioned in opposing relationship with the first substrate surface 115, as illustrated in FIG. 3B. The membrane 171 is interposed between the cover plate and the substrate. In addition, the cover plate and the substrate are aligned to provide fluid communication between each of the corresponding second-dimension microchannels of the substrate and cover plate through the pores of the membrane. Usually, a liquid-tight seal is formed between the cover plate, the membrane and the substrate such that fluid is confined to the microchannels and the pores of the membrane.

In operation, one or more fluids containing analyte molecules are introduced into the first-dimension substrate microchannel 119 from an external source through inlet port 137. A first motive force is provided by motive force means (not shown) in the direction defined from the inlet terminus 121 to the downstream terminus 123 of the first-dimension microchannel as indicated by arrow D1. The first-dimension substrate microchannel 119 may be adapted to perform a function such as molecular weight separation in order to sort analyte molecules according to molecular weight. In such a case, molecule weight of the analyte molecules may decrease along the length of the substrate microchannel. In other words, the analyte molecules become spatially resolved by molecular weight as the sample fluid flows through the first-dimension substrate microchannel. In addition, a second motive force is provided by a second motive force means (not shown) in the direction defined from the upstream terminus 122 to the downstream terminus 124 of the second-dimension microchannels as indicated by arrow D2. As a result, the fluid is directed into the second-dimension substrate microchannels. The second-dimension substrate microchannels 120 also perform one or more functions that differ from the function of the first-dimension substrate microchannel. For example, the second-dimension microchannel may be adapted to separate analyte molecules according to charge. In such a case, the charge of analyte molecules may decrease along the length of the second-dimension substrate microchannel. In other words, using the combination of the first-dimension and second-dimension microchannels allows analyte molecules to be spatially resolved by molecular weight in the direction of D1 and by charge in the direction of D2.

The pores 177 in the membrane allow fluid from the second-dimension substrate microchannels 120 to be conveyed to the corresponding second-dimension cover plate microchannels 158. When fluid is conveyed from the second-dimension substrate microchannels to the second-dimension cover plate microchannels, analyte molecules are digested by the attached moiety to form digested analyte components. The components of the digested analyte molecules retain their spatial resolution. By providing the appropriate motive forces in proper sequence and adapting the cover plate microchannels, first and/or second degree, to perform separation of the components formed through analyte molecules digestion, sequential delivery of such components may be effected through the outlet port. Optionally, subsequent analysis may be performed using known techniques such as MALDI-TOF mass spectrometry or by electrospray liquid chromatography and mass spectrometry.

It should be evident that the arrangement of the membrane in combination with microchannels allows all digested components from a given point in the initial multidimensional separation to be grouped in space and time. As a result, information with respect to a component of an analyte molecule is not lost from analyte digestion. In other words, the configuration of this microanalytical device provides at least one additional dimension of separation resulting in improved precision in biomolecular identification.

The materials used to form the substrates and cover plates in the microanalytical devices of the invention as described above are selected with regard to physical and chemical characteristics that are desirable for the functions to be carried out by the microanalytical device. For example, all device materials used should be chemically inert and physically stable with respect to any fluids or analyte molecules with which they come into contact, under the reaction conditions used (e.g., with respect to pH, electric fields, etc.). For use in chemical processes involving high temperatures, it is important that all materials be chemically and physically stable within the range of temperatures used. In all cases, the substrate must be fabricated from a material that enables formation of high definition (or high "resolution") features, i.e., microchannels, chambers and the like, that are of micron or submicron dimensions. That is, the material must be capable of microfabrication using, e.g., dry etching, wet etching, laser etching, molding, embossing, or the like, so as to have desired miniaturized surface features; preferably, the substrate is capable of being microfabricated in such a manner as to form features in, on and/or through the surface of the substrate. Microstructures can also be formed on the surface of a substrate by adding material thereto, for example, polymer channels can be formed on the surface of a glass substrate using photo-imageable polyimide. Suitable materials for forming the present devices include, but are not limited to, polymeric materials, ceramics (including aluminum oxide and the like), glass, metals, composites, and laminates thereof.

Polymeric materials are particularly preferred herein, and will typically be organic polymers that are either homopolymers or copolymers, naturally occurring or synthetic, crosslinked or uncrosslinked. Specific polymers of interest include, but are not limited to, polyimides, polycarbonates, polyesters, polyamides, polyethers, polyurethanes, polyfluorocarbons, polystyrenes, poly(acrylonitrile-butadiene-styrene)(ABS), acrylate and acrylic acid polymers such as polymethyl methacrylate, and other substituted and unsubstituted polyolefins, and copolymers thereof. Polyimide is of particular interest and has proven to be a highly desirable substrate material in a number of contexts. It has been demonstrated, for example, that polyimides exhibit low sorptive properties toward proteins, which are known to be particularly difficult to process in certain silicon dioxide-based systems. Polyimides are commercially available, e.g., under the tradenames Kapton®, (DuPont, Wilmington, Del.) and Upilex® (Ube Industries, Ltd., Japan).

The devices of the invention may also be fabricated from a "composite," i.e., a composition comprised of unlike materials. The composite may be a block composite, e.g., an A-B-A block composite, an A-B-C block composite, or the like. Alternatively, the composite may be a heterogeneous combination of materials, i.e., in which the materials are distinct from separate phases, or a homogeneous combination of unlike materials. As used herein, the term "composite" is used to include a "laminate" composite. A "laminate" refers to a composite material formed from several different bonded layers of identical or different materials. Other preferred composite substrates include polymer laminates, polymer-metal laminates, e.g., polymer coated with copper, a ceramic-in-metal or a polymer-in-metal composite. One preferred composite material is a polyimide laminate formed from a first layer of polyimide such as Kapton®, available from DuPont (Wilmington, Del.), that has been co-extruded with a second, thin layer of a thermal adhesive form of polyimide known as KJ®, also available from DuPont (Wilmington, Del.).

The present microanalytical devices can be fabricated using any convenient method, including, but not limited to, micromolding and casting techniques, embossing methods, surface micro-machining and bulk-micromachining. The latter technique involves formation of microstructures by etching directly into a bulk material, typically using wet chemical etching or reactive ion etching ("RIE"). Surface micro-machining involves fabrication from films deposited on the surface of a substrate. An exemplary surface micro-machining process is known as "LIGA." See, for example, Becker et al. (1986), "Fabrication of Microstructures with High Aspect Ratios and Great Structural Heights by Synchrotron Radiation Lithography Galvanoforming, and Plastic Moulding (LIGA Process)," *Microelectronic Engineering* 4(1):35–36; Ehrfeld et al. (1988), "1988 LIGA Process: Sensor Construction Techniques via X-Ray Lithography," *Tech. Digest from IEEE Solid-State Sensor and Actuator Workshop*, Hilton Head, SC; Guckel et al. (1991) *J. Micromech. Microeng.* 1: 135–138. LIGA involves deposition of a relatively thick layer of an X-ray resist on a substrate followed by exposure to high-energy X-ray radiation through an X-ray mask, and removal of the irradiated resist portions using a chemical developer. The LIGA mold so provided can be used to prepare structures having horizontal dimensions—i.e., diameters—on the order of microns.

A preferred technique for preparing the present microanalytical devices is laser ablation. In laser ablation, short pulses of intense ultraviolet light are absorbed in a thin surface layer of material. Preferred pulse energies are greater than about 100 millijoules per square centimeter and pulse durations are shorter than about 1 microsecond. Under these conditions, the intense ultraviolet light photo-dissociates the chemical bonds in the substrate surface. The absorbed ultraviolet energy is concentrated in such a small volume of material that it rapidly heats the dissociated fragments and ejects them away from the substrate surface. Because these processes occur so quickly, there is no time for heat to propagate to the surrounding material. As a result, the surrounding region is not melted or otherwise damaged, and the perimeter of ablated features can replicate the shape of the incident optical beam with precision on the scale of about one micron or less. Laser ablation will typically involve use of a high-energy photon laser such as an excimer laser of the $F_2$, ArF, KrCl, KrF, or XeCl type. However, other ultraviolet light sources with substantially the same optical wavelengths and energy densities may be used as well. Laser ablation techniques are described, for example, by Znotins et al. (1987) *Laser Focus Electro Optics*, at pp. 54–70, and in U.S. Pat. Nos. 5,291,226 and 5,305,015 to Schantz et al.

The fabrication technique that is used must provide for features of sufficiently high definition, i.e., microscale components, channels, chambers, etc., such that precise alignment—"microalignment"—of these features is possible, i.e., the laser-ablated features are precisely and accurately aligned, including, e.g., the alignment of complementary microchannels or microcompartments with each other, inlet and/or outlet ports with microcolumns or reaction chambers, detection means with microcolumns or separation compartments, detection means with other detection means, projections and mating depressions, grooves and mating ridges, and the like. It should be evident that features other than those described above may be ablated into either the substrate or the cover plate in order to conduct other chemical or biochemical processes, e.g., to increase the concentration of a particular analyte or chemical component prior to chemical processing in the reaction chamber or to remove unwanted, potentially interfering sample or reaction components.

Membranes suitable for use in the present inventive device require a carefully designed pore structure onto which a chemical altering moiety may be immobilized. Generally, such membranes have a generally opposing surface and a plurality of evenly spaced pores that allow fluid communication between the opposing surfaces. In the alternative, the pores may be positioned to correspond to the locations of the microchannels of the substrate and/or the cover plate. It is particularly desirable to ensure that there is no interconnectivity between the pores. Interconnected pores may compromise the performance of the microanalytical device by promoting uncontrolled migration of the fluid, thereby possibly decreasing the spatial resolution of analyte molecules or reducing the mobility of the analyte molecules in a desired direction.

Moreover, such membranes may or may not have an active control structure such as those described in U.S. Pat. No. 5,556,528 to Bohn et al. This patent discloses electric-field responsive membranes having an active control structure composed of at least one monomolecular layer. The one layer (and any additional monomolecular layers) may be carried on a surface of a support that, without the active control structure, permits target molecules to diffuse therethrough. Each monomolecular layer has substantially all its molecules in a closely packed assemblage where the molecules are generally aligned along their long axes and packed in the monomolecular layer to be within about one short axis molecular diameter of each other. Particularly preferred active control structures have three or more monomolecular layers, wherein pore diameters are formed therein in the nanometer range. Such a nanoporous support carrying the active control structure can form a permeability controllable barrier. In some instances, pores of membranes suitable for use with the invention have a diameter in the range of about 10 angstroms to about 500 angstroms.

The analyte altering moiety attached to the inner surface of the pore is selected according to the desired type of chemical alteration. For example, if the desired chemical alteration is oxidation, the analyte altering moiety is an oxidation agent. The analyte altering moiety may also be selected according to the analyte molecules. For example, for proteolytic applications, the chemical altering moiety may be an enzyme that specifically targets a particular peptidic structure or a commonly used proteolytic enzyme such as trypsin and pepsin. As another example, when it is desirable to engage in nucleic acid analysis, nuclease enzymes capable of nucleotidic digestion, e.g., endonucleases and exonucleases, may be used as the chemical altering moiety. Other digestive moieties are known to one of ordinary skill in the art as are methods of attaching analyte altering moieties to a surface such as an interior surface of a pore. Such methods include covalent or other types of chemical bonding either using direct or indirect attachment processes.

From the above description of the various embodiments of the invention, it is evident that the inventive microanalytical device provides a number of advantages over the previously known technology such as conventional two-dimensional gel electrophoresis. For example, because the microanalytical devices are easily manufacturable and may be made from low-cost materials, the microanalytical devices may be disposable. As a result, disadvantages associated with prior art devices are eliminated such as memory effects, cross contamination, and long washing sequences, because a fresh microanalytical device may be used for every sample. Moreover, even if treated as reusable, the microanalytical devices may be constructed to facilitate cleaning. In prior art devices, the interior surfaces of a conduit that are exposed to fluid samples are cleaned by flowing a cleaning fluid through the conduit. If the conduit has a small diameter, flushing is constrained by laminar fluid flow. As a result, long wash sequences are associated with such devices. The inventive microanalytical devices, however, may be constructed to allow the substrate of the microanalytical device to be separated from the cover plate, thereby exposing the microchannels. As a result, cleaning is not constrained by laminar flow and does not require long wash sequences. Moreover, a disposable membrane may be used for each new analysis in an otherwise nondisposable device. In other words, the inventive microanalytical device may be adapted to identify molecules with both the speed associated with approaches such as liquid chromatography and the resolution of two-dimensional gel-electrophoresis.

Variations of the present invention will be apparent to those of ordinary skill in the art. For example, because fluid flow control is an important aspect of the invention, known means for fluid control may represent integrated and/or additional features of the inventive microanalytical device. Such fluid flow control means include, but are not limited to, valves, motive force means, manifolds, and the like. Such fluid flow control means may represent an integrated portion of the inventive microanalytical devices or modular units operably connectable with the inventive microanalytical devices. Moreover, computerized controls may be employed in order control the motive means to preserve spatial resolution of analyte and to ensure sequential transport thereof in the microchannels. In addition, while the embodiments described herein include a substrate and a cover plate, it should be noted that additional substrates or microchannels may be included to provide an additional dimensional basis for analysis. It should be further evident that additional features such as apertures and microchannels may be formed in appropriate manner to ensure proper reaction conditions.

It is to be understood that while the invention has been described in conjunction with the preferred specific embodiments thereof, that the foregoing description is intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

What is claimed is:

1. A microanalytical device for analyzing a fluid sample containing at least one analyte molecule, comprising:
   a substrate having a substantially planar substrate surface and a substrate microchannel formed in the substrate surface, wherein the substrate microchannel extends from an upstream terminus to a downstream terminus;
   a cover plate having a substantially planar cover plate surface and a cover plate microchannel formed on the cover plate surface, wherein the cover plate surface is arranged over the substrate surface;
   an inlet port in fluid communication with the substrate microchannel;
   a membrane interposed between the substrate and the cover plate and having at least one pore sized to allow passage of the analyte molecule from the substrate microchannel to the cover plate microchannel, wherein the at least one pore is located downstream from the inlet port; and
   an analyte altering moiety attached to an interior surface of the at least one pore, wherein the moiety is capable of chemically altering the analyte molecule.

2. The microanalytical device of claim 1, wherein the substrate microchannel is substantially parallel to the cover plate microchannel.

3. The microanalytical device of claim 2, wherein the membrane has a plurality of pores each sized to allow passage of fluid sample from the substrate microchannel to the cover plate microchannel.

4. The microanalytical device of claim 1, wherein the analyte altering moiety is adapted to digest the analyte molecule to form at least two analyte components.

5. The microanalytical device of claim 4, wherein the cover plate microchannel is adapted to separate the at least two analyte components.

6. The microanalytical device of claim 4, wherein the analyte altering moiety is an enzyme.

7. The microanalytical device of claim 6, wherein the enzyme is a proteolytic enzyme.

8. The microanalytical device of claim 1, wherein each pore of the membrane has a diameter in the range of about 10 angstroms to about 500 angstroms.

9. The microanalytical device of claim 1, wherein the membrane comprises a support that permits the fluid sample to diffuse therethrough and at least one monomolecular layer carried on a surface of the support, the at least one monomolecular layer being at least a portion of an active control structure.

10. The microanalytical device of claim 9, wherein the active control structure is controlled electrophorectically, electroosmotically or by application of pressure.

11. The microanalytical device of claim 1, wherein the analyte molecule is a biomolecule.

12. The microanalytical device of claim 11, wherein the biomolecule is peptidic.

13. The microanalytical device of claim 11, wherein the analyte molecule is nucleotidic.

14. The microanalytical device of claim 1, wherein the analyte molecule is oliogomeric or polymeric.

15. The microanalytical device of claim 1, wherein the fluid sample contains a first analyte molecule and a second analyte molecule.

16. The microanalytical device of claim 15, wherein the substrate microchannel is adapted to separate the first and second analyte molecules.

17. The microanalytical device of claim 1, wherein the substrate microchannel is adapted to chemically alter the analyte molecule.

18. The microanalytical device of claim 17, wherein the substrate microchannel is adapted to digest the analyte molecule to form at least two analyte components.

19. The microanalytical device of claim 18, wherein the substrate is further adapted to separate the at least two analyte components.

20. The microanalytical device of claim 1, wherein the cover plate microchannel is adapted for fluid communication with a mass spectrometer to allow the fluid sample to be introduced thereto.

21. The microanalytical device of claim 1, wherein the substrate microchannel is adapted for fluid communication with a source of the fluid sample.

22. The microanalytical device of claim 1, wherein the substrate microchannel comprises a first-dimension microchannel and at least one second-dimension microchannel, each second-dimension microchannel fluidly communicating with the first-dimension microchannel.

23. The microanalytical device of claim 22, wherein the substrate microchannel comprises a plurality of second-dimension microchannels each fluidly communicating with the first-dimension microchannel at a different point.

24. The microanalytical device of claim 23, wherein all of the second-dimension microchannels are parallel to one another.

25. A method for chemically altering and transporting an analyte molecule in a fluid, comprising the steps of:

(a) introducing the molecule through an inlet port into a microchannel formed in a substantially planar substrate surface so that the molecule travels along the microchannel;

(b) transporting the molecule from the substrate microchannel in a non-parallel direction with respect to the substrate surface into a pore of a membrane, wherein the pore is located downstream from the inlet port;

(c) chemically altering the analyte molecule to form an altered molecule using a moiety attached to an interior surface of the pore; and (d) collecting the altered molecule from the pore on a cover plate microchannel formed on a substantially planar cover plate surface of a cover plate, wherein the substantially planar cover plate surface is in opposing relation to the substantially planar substrate surface.

26. The method of claim 25, wherein step (c) comprises digesting the analyte molecule using the moiety attached to the interior surface of the pore.

27. The method of claim 26, wherein the attached moiety comprises an enzyme.

28. The method of claim 27, wherein the attached enzyme is a proteolytic enzyme.

29. The method of claim 25, wherein step (b) comprises electrophoresis and/or pressure.

30. A method for identifying a plurality of biomolecules, comprising the steps of:

(a) providing a substrate having a substantially planar substrate surface, the substrate having a substrate microchannel formed in the substrate surface;

(b) spatially resolving the biomolecules along the substrate microchannel;

(c) transporting the biomolecules from the substrate microchannel in a non-parallel direction with respect to the substrate surface into pores of a membrane while preserving the spatial resolution of the biomolecules;

(d) digesting the biomolecule in the pores of the membrane to form biomolecular components;

(e) collecting the biomolecular components from the pores while preserving the spatial resolution of the biomolecular components on a cover plate microchannel formed on a substantially planar cover plate surface of a cover plate, wherein the substantially cover plate surface is in opposing relation to the substantially planar substrate surface; and (f) spatially resolving the biomolecular components in the cover plate microchannel.

* * * * *